United States Patent [19]

Huber et al.

[11] Patent Number: 4,529,545

[45] Date of Patent: Jul. 16, 1985

[54] ISOLATION OF CHEMICALLY UNSTABLE ANTIBIOTICS FROM FERMENTATION SOLUTIONS

[75] Inventors: Gerhard Huber, Kelkheim; Peter Schindler, Mörfelden-Walldorf, both of Fed. Rep. of Germany

[73] Assignee: Hoechst Aktiengesellschaft, Frankfurt am Main, Fed. Rep. of Germany

[21] Appl. No.: 443,130

[22] Filed: Nov. 19, 1982

[30] Foreign Application Priority Data

Nov. 21, 1981 [DE] Fed. Rep. of Germany ....... 3146190

[51] Int. Cl.$^3$ .................... C07D 487/04; A61K 31/40
[52] U.S. Cl. ....................... 260/245.2 T; 260/245.2 R
[58] Field of Search ............................... 424/274, 271; 260/245.2 T, 245.2 R

[56] References Cited

U.S. PATENT DOCUMENTS

| | | | |
|---|---|---|---|
| 3,962,427 | 6/1976 | Stark | 424/118 |
| 3,973,015 | 8/1976 | Hamill et al. | 424/246 |
| 3,993,748 | 11/1976 | Argoudelis et al. | 424/118 |
| 4,054,564 | 10/1977 | Hamill et al. | 424/246 |
| 4,221,870 | 9/1980 | Box | 260/245.2 T |
| 4,229,534 | 10/1980 | Kahan et al. | 260/245.2 T |
| 4,247,640 | 1/1981 | Kempf et al. | 260/245.2 T |
| 4,282,322 | 8/1981 | Kahan et al. | 260/245.2 T |
| 4,292,241 | 9/1981 | Tanaka et al. | 260/245.2 T |
| 4,318,916 | 3/1982 | Okamura et al. | 260/245.2 T |
| 4,404,218 | 9/1983 | Ito et al. | 260/245.2 T |

*Primary Examiner*—Nicholas S. Rizzo
*Attorney, Agent, or Firm*—Curtis, Morris & Safford

[57] ABSTRACT

A method for isolating a chemically unstable carbapenum antibiotic from a fermentation solution by adsorbing the antibiotic on an ion exchanger resin at the maximum of product formation, thus converting it to a stabilized form, and then separating the resin from the fermentation solution.

7 Claims, No Drawings

ISOLATION OF CHEMICALLY UNSTABLE ANTIBIOTICS FROM FERMENTATION SOLUTIONS

β-Lactam antibiotics having a carbapenem structure, for example the thienamycin and the olivanic acid group, and which have been produced by streptomyces strains, are distinguished by a particularly high antimicrobial activity and by a broad activity range. Antibiotics of this group are simultaneously efficient inhibitors or inactivators, respectively, of β-lactamases of different origin. Isolating these substances from fermentation solutions is extremely difficult because of their extreme chemical unstability. For example, the half-life of the chemical degradation of thienamycin in aqueous solutions at a medium pH (6-8), is from 0.3 to 6 hours, depending on the conditions applied (cf. J. Antibiot. 32, 1-12, 1979), olivianic acids have a half-life of from 4 to 27 hours (cf. J. Antibiot. 32, 295-304, 1979). Their instability still further increases in the case of higher concentrations thereof, which can be observed during their isolation and enrichment. As a result, a great portion of the antibiotic activity is lost in the course of the isolation process. These losses increase by the fact that the activity in the fermentation solution very quickly decreases after it has reached its maximum and upon completion of the product formation, which has to be attributed in particular to the increased instability of the carbapenem antibiotics at the slightly elevated fermentation temperature (28° C.-30° C.). Filtration of the streptomyces mycelium carried out generally at the beginning of the isolation process results in considerable losses in activity, in particular in the case of relatively large fermentation batches which cannot be cooled quickly enough. For example, the recovery of activity in the first enrichment step by means of ion exchangers usually performed in this group (cf. cited literature), amounts to 10-40%.

It was therefore desirable to stop fermentation processes of said antibiotics at maximum of the product formation and to convert the total activity to a stabilized form. It has now been found surprisingly that an interruption of the fermentation process at the moment desired and conversion to a stabilized form is reached by adsorbing the antibiotics on suitable ion exchanger resins at the maximum of product formulation and by separating the resin from the fermentation solution.

Adsorption can be carried out, for example, by adding to the fermentation solution an ion exchanger resin binding the antibiotic activity and by rapidly cooling the fermentation solution, for example, by dilution with cold water, to about 1° C.-10° C., preferably 1° C.-6° C.

A still more advantageous procedure consists in suspending the ion exchanger resin in cold water at 1° C.-10° C., preferably 1° C.-6° C., and to pump the fermentation solution into such a suspension, thus bringing out rapid cooling and an immediate fixation of the antibiotic activity. Thus, the fermentation solution is simultaneously diluted with water.

Suitable ion exchanger resins in the present case are anion exchangers, preferably those having a medium to strong basicity, a low degree of cross-linking and a porous structure such as, for example, Dowex 1×2, Amberlite IRA-401 S, Amberlite IRA-900.

The exchanger resin may be separated from the fermentation solution and the mycelium by sedimentation (decantation) from the fermentation solution diluted in the above manner. In a further embodiment, the diluted fermentation solution containing the ion exchanger and the mycelium is filtered through an appropriate sieve, for example a vibration sieve (for example Perflux ®), that retains the ion exchanger and allows the passage of the mycelium.

To obtain a sedimentation time as short as possible, the ion exchanger should be chosen such that the density of the resin is far greater than that of the mycelium. Commercial resins moreover should have a grain diameter as great as possible, for example, of from 20 to 50 mesh, corresponding to 300-800 microns. When using an appropriate resin and when proceeding in the above manner, more than 90% of the activity produced in the fermentation solution are bound to the ion exchanger. The resin may be further processed immediately in usual manner or it may be deep-frozen after suction-filtration of the excess liquid until it is further processed and can be stored at a temperature of about −20° C. Antibiotics bound in this way are stable for at least 2-3 months.

To isolate the antibiotic activity, the ion exchanger resin is eluted in a known manner using salt solutions, for example sodium chloride, sodium acetate or potassium chloride, while adding an organic solvent miscible with water such as methanol, isopropanol or acetone, preferably at a concentration of from 20 to 80%, to improve the elution yield, which may amount to about 55-80%.

The total yield of the first purification step amounts, consequently, to about 50-75%, referred to the activity in the fermentation solution.

The activity of the thienamycin and olivanic acid antibiotics can be determined in a conventional manner by microbiologic tests (agar diffusion test, turbidimetric test) using suitable test strains, for example Escherichia coli or Bacillus subtilis. A suitable rapid test consists in determining the β-lactamase inhibitor action, for example by means of the new chromogenic β-lactamase substrates PADAC and CENTA (cf. P. Schindler et al., Abstracts, 21th Interscience Conference on Antimicrobial Agents and Chemotherapy, Chicago, 1981). The activity determined according to these methods is indicated as enzyme inhibitor units (UE 50/ml).

The following examples serve to illustrate the invention:

EXAMPLE 1

10 liters of fermentation solution of the strain Streptomyces Y 5633 A which produces several olivanic acid components and which reaches the maximum of activity, measured in enzyme inhibitor units, e.g. 15 UE 50/ml corresponding to UE 50, after 42 hours of fermentation (cf. J. Antibiot. 32, 295-304, 1979), are combined with 300 g of the anion exchanger resin Dowex 1×4, 20-50 mesh, while adding cold water with stirring and simultaneously cooling to 6° C. After 30 minutes, the fermentation solution is filled into a funnel-shaped receptacle with a bottom outlet and the anion exchanger resin is allowed to settle. The resin withdrawn at the bottom upon completion of the sedimentation process is washed with water to remove the mycelium residues by decantation and is further processed in a conventional manner, for example, by elution. The resin contains 138,000 UE 50 (92%), while 12,000 UE 50 (8%) are measured in the separated fermentation solution. The adsorbate obtained is treated with 1.2 l of a solution of 6% KCl in 50% aqueous acetone, while cooling and stirring, and the resin is separated by filtration after 3 hours. The elution solution contains 93,000 UE 50 (62%) and may be further processed in a conventional manner.

EXAMPLE 2

Immediately after the maximum activity of 22.0 UE 50/ml (corresponding to 3,850,000 UE 50) has been reached, 175 liters of fermentation solution of the Streptomyces strain Y 5633 A are pumped through a bottom valve into a receptacle containing 6 l of the anion exchanger Amberlite IRA-401 S, 20–50 mesh, suspended in 400 l of water of 6° C. After stirring for one hour, the resin is allowed to settle for about 30 minutes and is withdrawn through the bottom valve of the collecting receptacle by passing over a sieve having an inner mesh width of 150μ. The exchanger resin retained on the sieve is washed with cold water (6° C.) in a receptacle in order to remove the mycelium portions by decantation, and is then submitted to suction in order to dry its surface. The resin (3.6 kg) contains 3,620,000 UE 50 (94%) and the fermentation solution contains 230,000 UE 50 (6%).

The adsorbate obtained can be stored at −20° C. at least 2 months without loss of activity. For elution purposes, the ion exchanger resin is filled in a column provided with a cooling jacket, and is eluted with cooling (6° C.) using 6% of potassium chloride in 50% of aqueous acetone. Fractions of 500 ml are tested using the inhibitor test. The main activity (2,462,000 UE 50=68%) is contained in the fractions 12-20. The fractions are combined, concentrated to 0.9 l in a high vacuum, and introduced into a cooled column containing 6 liters of the adsorption resins Diaion HP-20, and the activity is eluted with cold water. The active salt-free fractions (No. 10–14) containing 2,136,000 UE 50 (59%) are combined and lyophilized. The crude antibiotics mixture obtained is further purified in known manner.

EXAMPLE 3

The streptomyces strain Y 5633 A producing olivanic acids is cultivated in the conventional manner in 3 liters of culture medium and 38 hours later, after the maximum of the product formation has been reached, the fermentation solution is added to a suspension of 90 g of Amberlite IRA-401 S, 20–50 mesh, in 6 liters of water cooled to 4° C. The resin is separated in the manner described in Example 1. It contains 90% of the activity measured in the fermentation solution. In order to elute the activity, Amberlite IRA-401 S is filled in a column (2.5×30 cm), and the activity is eluted using a linear gradient of 50% of aqueous acetone and 8% of KCl in 50% of aqueous acetone (fraction size 20 ml). The main activity is contained in the fractions 11-21, the elution yield is 55%.

What is claimed is:

1. A method for rapidly isolating a chemically unstable carbapenem antibiotic from a fermentation solution containing mycelium, which method comprises absorbing said antibiotic on an anion exchange resin, thereby converting it to a stabilized form, by contacting said fermentation solution, without prior separation of said mycelium therefrom, with said anion exchange resin at the maximum of antibiotic formation, and then separating the resin from the fermentation solution.

2. A method as in claim 1 wherein said anion exchange resin is of medium to strong basicity.

3. A method as in claim 2 wherein said resin has a particle size of 20-50 mesh.

4. A method as in claim 1 wherein said anion exchange resin is added to said solution at the maximum formation of antibiotic and the mixture is then rapidly cooled.

5. A method as in claim 1 wherein, at the maximum formation of antibiotic, said solution is introduced into a suspension of said resin in cold water.

6. A method as in claim 1 wherein said resin is separated from the fermentation solution by sedimentation.

7. A method as in claim 1 wherein said resin is separated from the fermentation solution by filtration in a sieve retaining said resin and passing said mycelium contained in the solution.

* * * * *